(12) United States Patent
Michael et al.

(10) Patent No.: US 11,385,214 B2
(45) Date of Patent: Jul. 12, 2022

(54) STRATIGRAPHIC BOUNDARIES IDENTIFICATION FROM CHEMOSTRATIGRAPHIC INTERVALS IN WELL LOGS BASED ON FIRST AND SECOND DERIVATIVES

(71) Applicant: Saudi Arabian Oil Company, Dhahran (SA)

(72) Inventors: Nikolaos A. Michael, Abqaiq (SA); Neil W. Craigie, Dhahran (SA); Christian Scheibe, Dammam (SA); Rainer Zuhlke, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 668 days.

(21) Appl. No.: 16/101,918

(22) Filed: Aug. 13, 2018

(65) Prior Publication Data

US 2020/0049685 A1 Feb. 13, 2020

(51) Int. Cl.
*G01N 33/24* (2006.01)
*G01V 1/30* (2006.01)
(Continued)

(52) U.S. Cl.
CPC .......... *G01N 33/24* (2013.01); *G01V 1/301* (2013.01); *G01V 3/38* (2013.01); *G01V 11/00* (2013.01); *G01V 99/005* (2013.01); *G06F 17/18* (2013.01)

(58) Field of Classification Search
None
See application file for complete search history.

(56) References Cited

U.S. PATENT DOCUMENTS

2009/0254283 A1* 10/2009 Jacobi .................... G01V 11/00
702/11
2014/0214324 A1* 7/2014 Freedman ................ G01V 5/08
702/8

(Continued)

OTHER PUBLICATIONS

Craigie, Neil W.; Rees, Andrew; MacPherson, Keith; Berman Seth; Chemostratigraphy of the Ordovician Sarah Formation, North West Saudi Arabia: An integrated approach to reservoir correlation; Aug. 12, 2016; Marie and Petroleum Geology 77, ppg. 1056-1080 (Year: 2016).*

(Continued)

*Primary Examiner* — Arleen M Vazquez
*Assistant Examiner* — Terence E Stifter, Jr.
(74) *Attorney, Agent, or Firm* — Fish & Richardson P.C.

(57) ABSTRACT

An elemental analysis of rock samples from outcrop sections or wells is performed. Data quality checks, data analysis, and filtering are performed on the rock samples, including de-spiking of elemental profiles and elemental ratios. First and second derivatives for the elemental profiles and the elemental ratios are calculated. Samples and depths that exceed thresholds are determined. The process is repeated for the elemental profiles and the elemental ratios that are related with boundary determination and carbonate or siliciclastic sediments. Additional filters are applied to at least a subset of the elemental profiles and elemental ratios that are related with boundary determination and carbonate or siliciclastic sediments to enhance the boundary identification. Possible boundaries in depths of the outcrop sections or wells are determined by summarizing the additionally filtered elemental profiles and the additionally filtered elemental ratios.

14 Claims, 7 Drawing Sheets

(51) Int. Cl.
G01V 3/38 (2006.01)
G01V 11/00 (2006.01)
G06F 17/18 (2006.01)
G01V 99/00 (2009.01)

(56) References Cited

U.S. PATENT DOCUMENTS

| | | | | |
|---|---|---|---|---|
| 2015/0233846 | A1* | 8/2015 | Locklair | G01N 23/223 378/45 |
| 2016/0018556 | A1* | 1/2016 | Montgomery | G01N 33/24 702/2 |
| 2017/0183962 | A1* | 6/2017 | Far | G01V 3/18 |
| 2019/0179049 | A1* | 6/2019 | Lubbe | E21B 49/02 |

OTHER PUBLICATIONS

Hill, E. June; Uvarova, Yulia; Identifying the nature of lithogeochemical boundaries in drill holes; Oct. 28, 2017; Journal of Geochemical Exploration 184 p. 167-178 (Year: 2017).*
International Search Report and Written Opinion issued in International Application No. PCT/US2019/045414 dated Nov. 27, 2019, 17 pages.
Rowe et al., "The quantification and application of handheld energy-dispersive xray fluorescence (ED-XRF) in mudrock chemostratigraphy and geochemistry," Chemical Geology, vol. 324-325, Sep. 1, 2012, 10 pages.
Pozzi et al., "Wellsite Chemostratigraphy in the Petroleum Province of Anadarko Basin: How Thermal Pulses, Deposition and Diagenesis Influence Hydrocarbon Accumulation," Proceedings of the 5th Unconventional Resources Technology Conference, Jan. 1, 2017, 12 pages.
Rowe et al., "Core Chemostratigraphy and Elemental Geochemistry Along a Dip-Section, Pearsall Formation, Lower Cretaceous, Central to South Texas," Proceedings of the 3rd Unconventional Resources Technology Conference, Jan. 1, 2015, 5 pages.
Andrew et al., "Application of chemostratigraphy to petroleum exploration and field appraisal: An example from the Surat Basin," SPE 37008, SPE Asia Pacific Oil & Gas Conference, Oct. 28-31, 1996, 9 pages.
Nehme, "Geochemistry and High-Resolution Chemostratigraphy of the Haynesville Formation, East Texas," thesis for degree of Masters of Science at the University of Texas at Austin, May 2015, 102 pages.
Buller et al., "A new mineralogy cuttings analysis workflow for optimized horizontal fracture-stage placement in organic shale reservoirs," SPE-170908, SPE Annual Technical Conference and Exhibition, Oct. 27-29, 2014, 28 pages.
Craigie et al., "Chemostratigraphy and biostratigraphy of Devonian, Carboniferous and Permian sediments encountered in eastern Saudi Arabia: an integrated approach to reservoir correlation," Marine and petroleum Geology, V. 72, Apr. 2016a, 23 pages.
Craigie et al., "Chemostratigraphy of the Ordovician Sarah Formation, North West Saudi Arabia: an integrated approach to reservoir correlation," Marine and petroleum Geology, V. 77, Nov. 2016b, 25 pages.
Ellis and Singer, "Well Logging for Earth Scientists," Springer, Jun. 29, 2007, 699 pages.
Gezeery et al., "A high-resolution chemo stratigraphy application in carbonates—a case study in the Cretaceous Mishrif reservoir, Minagish Field, Kuwait," UPC 13875, International Petroleum Technology Conference, Dec. 2009, 16 pages.
Lanning and Johnson, "Automated identification of rock boundaries: An application of the Walsh transform to geophysical well-log analysis," Geophysics vol. 48, No. 2, Feb. 1983, 9 pages.
MacDonald et al., "Using elemental geochemistry to improve sandstone reservoir characterization: A case study from the Unayzah A interval of Saudi Arabia," SPWLA 51st Annual Logging Symposium, Jun. 19-23, 2010, 16 pages.
Pearce et al., "Chemostratigraphy of the Upper Carboniferous Schooner Formation, southern North Sea," cited in Collinson, J.D. Evans, Holliday, D.W. and Jones, N.S. (eds.), Carboniferous hydrocarbon resources: the southern North Sea and surrounding onshore areas. Yorkshire Geological Society, Occasional Publications series, vol. 7, Feb. 23, 2005a, 18 pages.
Pearce et al., "Stratigraphy of the Upper Carboniferous Schooner Formation, Southern North Sea: Chemostratigraphy, mineralogy, paylnology and Sm-Nd isotope analysis," in Carboniferous hydrocarbon resources: the southern North Sea and surrounding onshore areas, vol. 7, Occasional Publication Series of the Yorkshire Geological Society, 2005, 18 pages.
Ratcliffe et al., "A regional chemostratigraphically-defined correlation framework for the late Triassic TAG-I Formation in Blocks 402 and 405a, Algeria," Petroleum Geoscience vol. 12, No. 1, Feb. 2006a, 12 pages.
Ratcliffe et al., "An example of alternative correlation techniques in a low-accommodation setting, nonmarine hydrocarbon system: The (Lower Cretaceous) Mannville Basal Quartz succession of southern Alberta," AAPG Bulletin, V. 88, No. 10, Oct. 2004, 14 pages.
Ratcliffe et al., "Chemostratigraphy of a channalised turbidite system, the Britannia Formation (lower Cretaceous), Brodgar Field and surrounding areas, North Sea," AAPG Annual Convention, Apr. 9-12, 2006, Feb.-Mar. 2014, 1 pages.
Ratcliffe et al., "Enhanced reservoir characterization of the Triassic Argilo Greseux-Inferieur, Algeria using high resolution chemostratigraphy," Extended abstract, AAPG Conference May 11-14, 2003, 5 pages.
Reyment, "A quantitative procedure for chemostratigraphy," Stratigraphy vol. 1, No. 1, 2004, 2 pages.
Sano et al., "Chemostratigraphy of the Haynesville Shale," in Hammes, U. and Gale, J. (eds.), Geology of the Haynesville Gas Shale in East Texas and West Louisiana, U.S.A., AAPG Memoir 105, 2013, 18 pages.
Serra, "Fundamentals of well-log interpretation—1. The acquisition of logging data," Development in Petroleum Science, 15 A Elsevier, May 1984, 435 pages.
Wright et al., "The application of chemostratigraphic techniques to distinguish compound incised valleys in low-accommodation incised-valley systems in a foreland-basin setting: An example from the Lower Cretaceous Manville Group and Basal Colorado Sandstone (Colorado Group), western Canadian Sedimentary Basin," SEPM Special Publication No. 94, Jan. 2010, 18 pages.
Ye et al., "Rapid and Consistent Identification of Stratigraphic Boundaries and Stacking Patterns in Well Logs—An Automated Process Utilizing Wavelet Transforms and Beta Distribution," SPE-183860-MS, presented at the SPE Middle East Oil & Gas Show and Conference, Mar. 6-9, 2017, 24 pages.
GCC Examination Report in Gulf Cooperation Council Appln. No GC 2019-38088, dated Oct. 21, 2020, 4 pages.
GCC Examination Report in Gulf Cooperation Council Appln. No. GC 2019-38088, dated May 29, 2021, 4 pages.

* cited by examiner

STRATIGRAPHIC BOUNDARIES IDENTIFICATION FROM CHEMOSTRATIGRAPHIC INTERVALS IN WELL LOGS BASED ON FIRST AND SECOND DERIVATIVES

BACKGROUND

The present disclose applies to the field of geology, and chemostratigraphy in particular. Chemostratigraphy is an established reservoir correlation technique involving the applications of inorganic geochemical data.

The aim of most chemostratigraphy projects is to identify boundaries and zones based on changes in specific elements' concentrations and ratios. These zones can then be correlated between adjacent wells and field outcrop sections. While elements used in studies can include silicon (Si) (for example, from quarz), potassium (K), sodium (Na), and calcium (Ca) (for example, from feldspars or in carbonate rocks), other elements can be used. Elements can be analyzed, for example, using inductively coupled plasma mass spectrometry (ICP-MS), optical emission spectrometry (OES), and x-ray fluorescence (XRF). Analysis can also use other analytical techniques, including techniques associated with borehole tools. For example, the other analytical techniques can include laser-induced breakdown spectroscopy (LIBS), scanning electron microscopy with energy dispersive X-ray spectroscopy (SEM/EDX), and atomic absorption spectroscopy (AAS).

Systematic trends in elements and elemental ratios can be used to identify boundaries when the elements and elemental ratios are plotted or analyzed in profile form. While some studies may analyze over 50 elements, which can result in the generation of hundreds of different ratios related to the elements, most chemostratigraphic schemes are based on variations on 4-12 key or index elements/ratios. A recurrent problem is that elements and ratios can number over 200, making it a time-consuming process for the geologist to identify key parameters to be utilized for chemostratigraphic purposes and that provide meaningful stratigraphic subdivisions. Manual processing and analysis procedures of chemostratigraphic datasets can take up to several weeks to months. For example, current approaches may require significant time and resources to process hundreds or thousands of elements and elemental ratio profiles.

SUMMARY

The present disclosure describes techniques that can be used for identifying stratigraphic boundaries from chemostratigraphic intervals in well logs based on first and second derivatives. In some implementations, a computer-implemented method includes the following. An elemental analysis of rock samples from outcrop sections or wells is performed. Data quality checks, data analysis, and filtering are performed on the rock samples, including de-spiking of elemental profiles and elemental ratios. First and second derivatives for the elemental profiles and the elemental ratios are calculated. Samples and depths that exceed thresholds are determined. The process is repeated for the elemental profiles and the elemental ratios that are related with boundary determination and carbonate or siliciclastic sediments. Additional filters are applied to at least a subset of the elemental profiles and elemental ratios that are related with boundary determination and carbonate or siliciclastic sediments to enhance the boundary identification. Possible boundaries in depths of the outcrop sections or wells are determined by summarizing the additionally filtered elemental profiles and the additionally filtered elemental ratios. The techniques described in this disclosure can include the use of principal component analysis (PCA), for example, to derived variables to place chemostratigraphy boundaries.

An example follows of a workflow for a quick-look evaluation of chemostratigraphic and petrophysical data analysis within a subsurface. This workflow can use first and second derivatives of chemostratigraphic elemental profiles from well logs to subdivide rock formations in the subsurface into defined units in a fast and efficient way. The workflow can include steps to pick units based on the chemical signatures, including: 1) tracking the change in (rather than absolute values of) elemental ratios, and counting the number of elemental and element ratio profiles in which changes in log motifs exceed specific thresholds; 2) checking elemental and element ratio profiles to determine whether the profiles contribute to the variability and boundary identification; and 3) based on specific criteria of lithology or provenance identification or both, assigning weights to the elements/ratios to identify the most important boundaries. Prominent geological boundaries, for example, can reflect abrupt changes in quantities of most of the elements/ratios that characterize zones. Similar approaches can be used with petrophysical log data.

Techniques described in the present disclosure can include the following. Derivatives used to identify geological boundaries can be implemented in a software package. Elements can be weighted based on their geological significance, which can provide benchmarking data and can contribute in general workflows. Data can be summarized and sorted to determine the importance and overall contribution in the workflow.

The previously described implementation is implementable using a computer-implemented method; a non-transitory, computer-readable medium storing computer-readable instructions to perform the computer-implemented method; and a computer-implemented system comprising a computer memory interoperably coupled with a hardware processor configured to perform the computer-implemented method/the instructions stored on the non-transitory, computer-readable medium.

Implementations described in this disclosure can realize one or more of the following advantages. First, automatized techniques can be used to guide geologists and bypass cumbersome processing. Second, automated techniques can allow entire data sets to be processed in seconds, identifying boundaries based on significant increases or decreases in particular elements and ratio profiles. Third, the techniques can guide the identification of stratigraphic boundaries within well logs based on chemical signatures. Fourth, techniques can be incorporated into standard workflows for operations by performed by research and exploration entities. Fifth, the techniques can be applied to any wells, any field, any lithology, surface and subsurface data, for example, that include elemental ratios and profiles, different stable isotope data and profiles, and depth-calibrated continuous numerical rock characterization parameters.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

Like reference numbers and designations in the various figures indicate like elements.

DETAILED DESCRIPTION

The present disclosure describes techniques for identifying stratigraphic boundaries from chemostratigraphic intervals in well logs based on first and second derivatives. Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

In some implementations, identifying geological intervals based on changes of properties can include statistics for, and the analysis of, elemental profiles and ratios. Elemental profiles refer to the elemental concentrations or ratios between rock samples taken from wellbores or field outcrops versus vertical distances or depths in the subsurface. Depths can also apply, for example, to elevations for outcrop studies. Outcrop sections refer to exposed geological layers on the surface of the earth that cover specific periods of the geologic history.

Elemental data can be derived, for example, from x-ray fluorescence (XRF) or inductively coupled plasma (ICP) analysis. The elemental data can reflect variations in mineralogy that are related to changes in sedimentary provenance, depositional environment, and weathering/diagenesis. The techniques described in the present disclosure are not limited to geochemical data generated by ICP or XRF, but can be applied to all types of geochemical data regardless of the data's analytical origin (for example, from borehole tools). Chemostratigraphy can be used to identify these changes in order to identify intervals with unique geochemical signatures that can be correlated between adjacent wells or field outcrop sections. The analysis of large data sets of elemental data can expedite processes for compiling and statistically analyzing all elements and predefined elemental ratios. This can help geologists in identifying the best geological boundaries based on the analysis. In some implementations, techniques can include various workflows, such as a workflow that includes the following steps.

In a first step, quality checks can be performed on each of the elemental profiles and elemental ratios. For example, the quality checks can identify (and remove) outliers that can mask the true chemical signals. The outliers can include, for example, anomalous values of particular elements recorded in a small number of samples. Performing the quality checks can help to assure better quality results that would otherwise be possible.

For example, the quality checks can identify outliers and spikes that can indicate poor quality data that may affect (for example, skew) overall results. In some implementations, each sample's value can be compared with a mean and various standard deviations, such as based on a base signal, and a value given can be removed if determined to be anomalous. For example if a particular sample is recording five standard deviations greater than or less than the mean (or a base signal), then the sample may be removed and replaced with an averaged value. Outliers and spikes can theoretically be real, however such values are usually associated with errors, such as errors that occur during analysis.

In a second step, filters can be applied to the data, such as filters that can be used in de-spiking and normalization, or to minimize or eliminate induced statistical errors in the dataset. For example, some outliers and spikes may be caused by poor data quality rather than real values. Filters that are applied to outliers and spikes can help in data smoothing.

In a third step, first and second derivatives of the elemental profile and ratios can be calculated. The absolute data and the first and second derivatives can then be compared for each elemental profile.

Figure 1A:
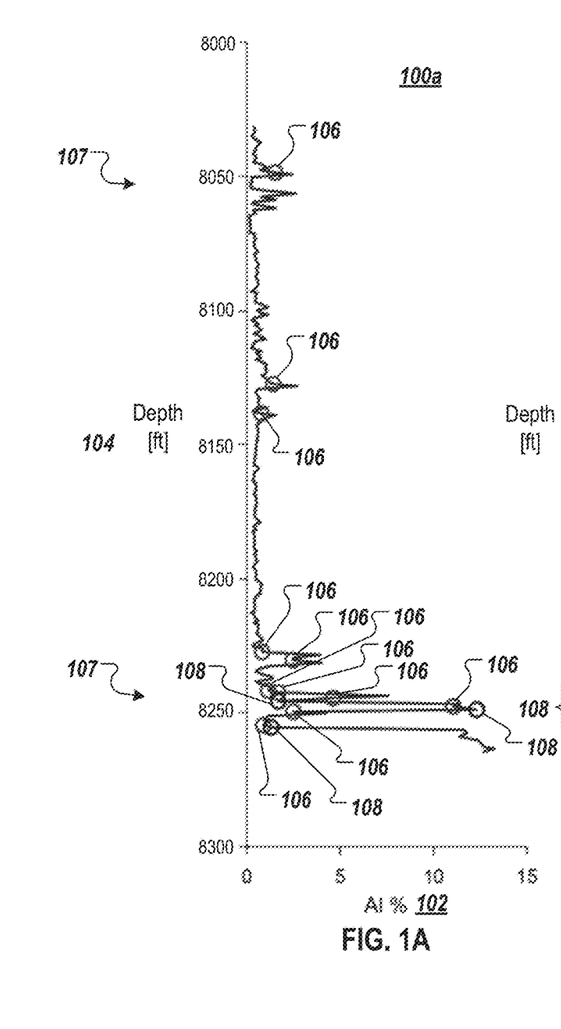
FIG. 1A is a graph showing a single elemental profile, according to some implementations of the present disclosure.
Figures 1B, 1C:
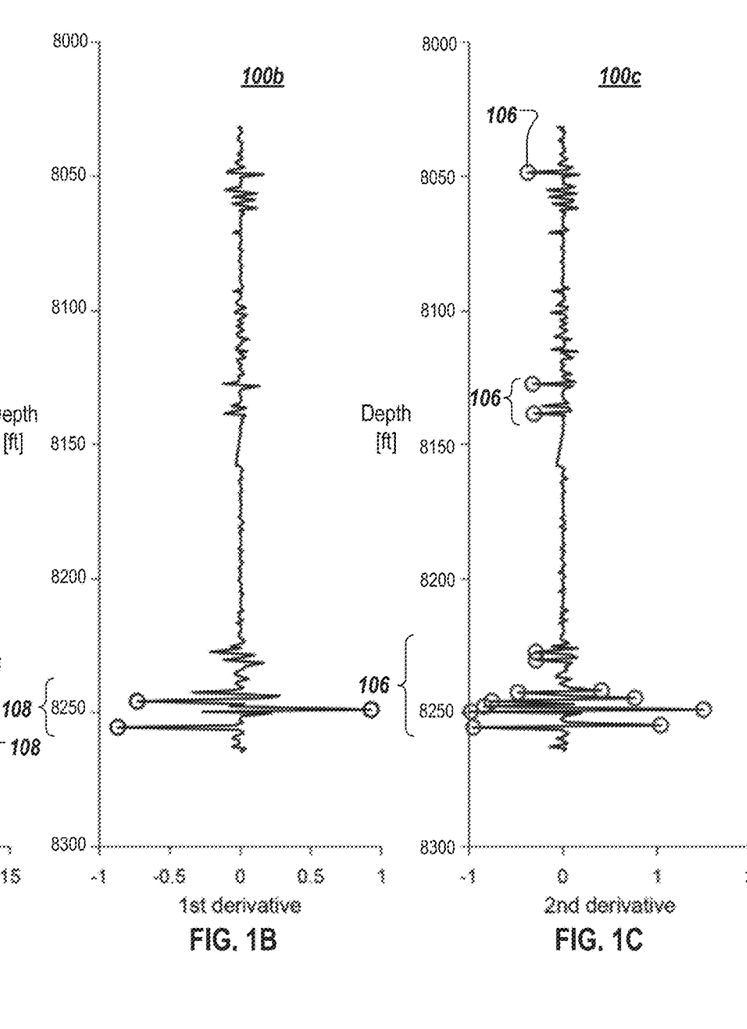
FIG. 1B is a graph showing a first derivative of the single elemental profile, according to some implementations of the present disclosure.
FIG. 1C is a graph showing a second derivative of the single elemental profile, according to some implementations of the present disclosure.

FIG. 1A is a graph showing a single elemental profile 100a, according to some implementations of the present disclosure. FIG. 1B is a graph showing a first derivative 100b of the single elemental profile 100a, according to some implementations of the present disclosure. The first derivative can be interpreted as an instantaneous rate of change. For example, first derivative 100b shown in FIG. 1B has been computed after de-spiking and normalization. FIG. 1C is a graph showing a second derivative 100c of the single elemental profile 100a, according to some implementations of the present disclosure. The second derivative 100c indicates an instantaneous rate of change in the first derivative.

Referring to FIG. 1A, for example, the single elemental profile 100a shows a single element (for example, Al) as a percentage of abundance 102 (X-axis) versus depth 104 (Y-axis). The data that is shown in FIG. 1A is quality checked and de-spiked. Circles 106 and 108 point out sample points where significant changes occur based on the first and second derivative, respectively, as in FIGS. 1B and 1C. FIG. 1B shows the first derivative of the same data after de-spiking and normalizing. The first derivative can be calculated by the difference of each sample from the previous one divided by the difference in depth. The circles 108 mark samples where the derivatives exceed a particular threshold (in this case ±2 standard deviations from the mean). FIG. 1C shows the second derivative of the data illustrating the acceleration of change. The circles 106 denote where the value of the second derivatives exceed a particular threshold (in this case ±2 standard deviations from the mean of the value).

Samples depths can be recorded for depths at which changes in the derivatives exceed a threshold. For example, samples that exceed one standard deviation from the median value of the first and second derivatives can be recorded as potential boundaries 107. Thresholds can alternatively be set at two standard deviations or any other threshold that a geologist sees fit for a particular study. Samples that exceed specific thresholds can be counted, and their depths can be assigned to possible boundaries. In FIGS. 1A-1C, circles 108 refer to abrupt changes in the first derivative and circles 106 refer to abrupt changes in the second derivative variations. Elemental compositions can be derived based on an analysis of rock samples and the first derivative.

The first derivative can identify a rate of change along an element or element ratio profile, and can be calculated for each data point/sample along the profile. In some implementations, the first derivative can be calculated as a difference of composition/measurement between adjacent data points/samples along the profile, divided by a vertical separation between the two points. The first derivative can capture the rate of change between the points and can be particularly effective at identifying significant changes. In some implementations, the first point along the profile can be assigned a zero value.

Distances between points can be controlled (for example, selectively chosen) so that distances are regular and have sufficient size to provide meaningful results. Distances that are irregular or too small can affect derivative calculations and can cause unreliable results. As a result, successful calculations of derivative can occur when a sampling step (for example, the distance between depths adjacent data points) is constant. If the sampling step is too small, or if two samples have the same depth, one of the data points can be omitted, or the data points can be combined (for example, averaged), or a pseudo-minimum sampling step (or distance between the data points) can be assigned. If distances between points are not controlled, for example, the techniques may produce boundaries that have no geological meaning.

As an example, a goal of the analysis is to understand chemical changes between sample points in a well. Derivatives can be calculated between points (or samples). To determine the first and second derivatives, the difference between samples can be divided by their vertical distance. For the technique to be optimized for best results, the distance/spacing is to be constant. Irregular spaces between samples can occur when spacing between sample points is not constant. An ideal distance, for example, is a constant one-foot distance. In practice, sampling spaces can be irregular. However, if sampling distances deviate very much from a median distance between samples (for example, one standard deviation) those samples can have highly irregular spacing. An example of highly irregular spacing is 2 cm, 5 cm, 1 m, 3 cm, and 30 cm. In this case, the analysis can select the spacing between the samples rather than changes in provenance or changes in the chemical composition with depth. Therefore, for the analysis to work best, the sample spacing needs to be somewhat regular or constant, while allowing some degree of freedom. Highly irregular spacing will affect the results. Analysis results can also suffer when very small spacing is used.

When a very small median spacing between points occurs, the spacing for particular two samples can be smaller than two standard deviations from the median spacing of the data set. As a result, the analysis can result in anomalous high (or low) derivative values that correspond to the spacing, rather than changes in composition that the analysis is trying to capture.

The second derivative can identify an acceleration of change between two sample points along a same profile. The second derivative can be calculated as a difference of the first derivative of adjacent points divided by their vertical separation.

The process of calculating and analyzing the first and second derivatives can be repeated for all the elemental or elemental ratio profiles. The analysis of the first and second derivatives can work with any number of ratios or combination of elements to locate statistical variations of the first and second derivative. Once analysis has been completed for all relevant ratios or combination of elements, the methodology can include recording the number of times a data point/sample that relates to depth from a specific well or outcrop section has been observed, and a possible boundary can be assigned at that point. The more often that a specific sample/depth has been assigned as a possible boundary, the stronger the indication that it represents a geological boundary. This analysis process can also be used with petrophysical logs (for example, gamma ray, sonic, and density logs) that are standard in the oil industry.

Boundaries that have been assigned as possible boundaries can be categorized depending on the frequency of occurrences. Boundaries that are assigned as boundaries for 50% of the elements, for example, can be designated as greater-likelihood boundaries. Other boundaries that are less obvious (for example, detected in fewer ratios or profiles) can be considered as moderate-likelihood boundaries, representing possible boundaries. Between individual boundaries, chemical signals can be relatively monotonous without large variations.

A fourth step can include the application of filters on the use of elements and ratios depending on their importance in boundary recognition. The elements and ratios can be sorted according to the number of boundaries recognized for each well, with the more prominent elements shown first.

The elements/ratios that are determined can change with each study and can depend exclusively on the mineralogical composition of the study samples. Elements and ratios that are deemed unimportant for chemostratigraphic characterization and correlation in a given project can be excluded from the derivatives analysis since the elements and ratios may dilute the signal and boundary identification.

Figure 2A:
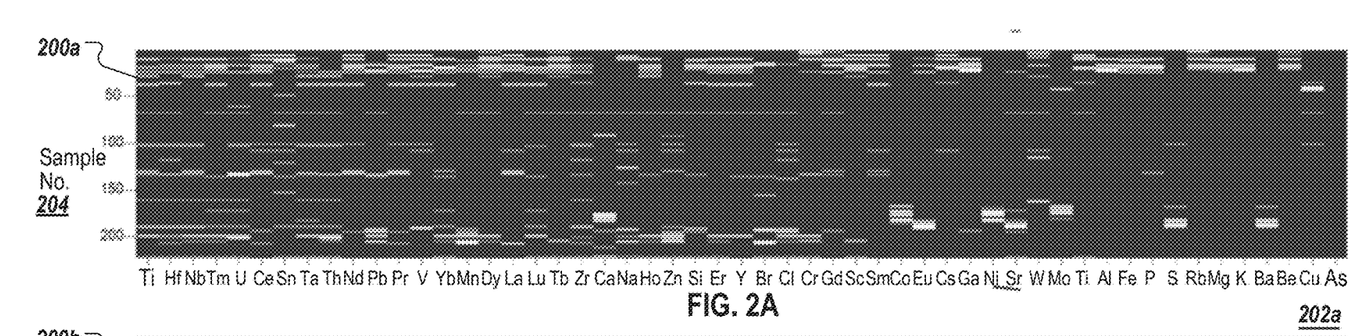
FIGS. 2A-2C are graphs showing elements detected at various depths, according to some implementations of the present disclosure.
Figure 2B:
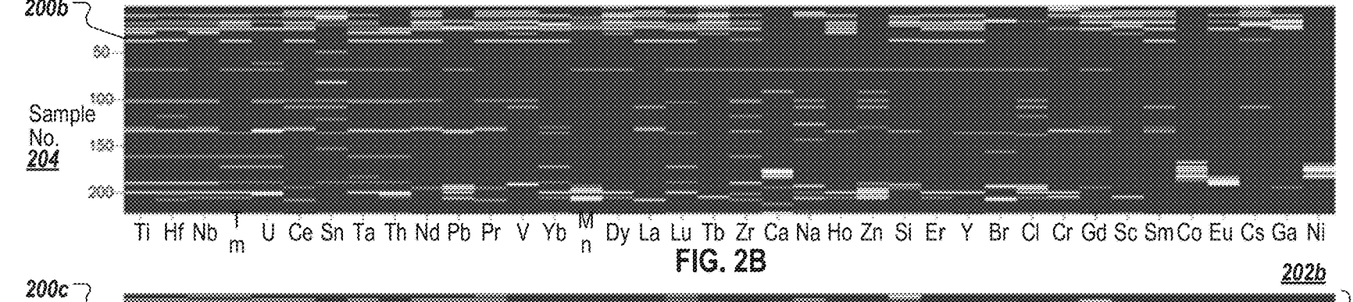
Figure 2C:
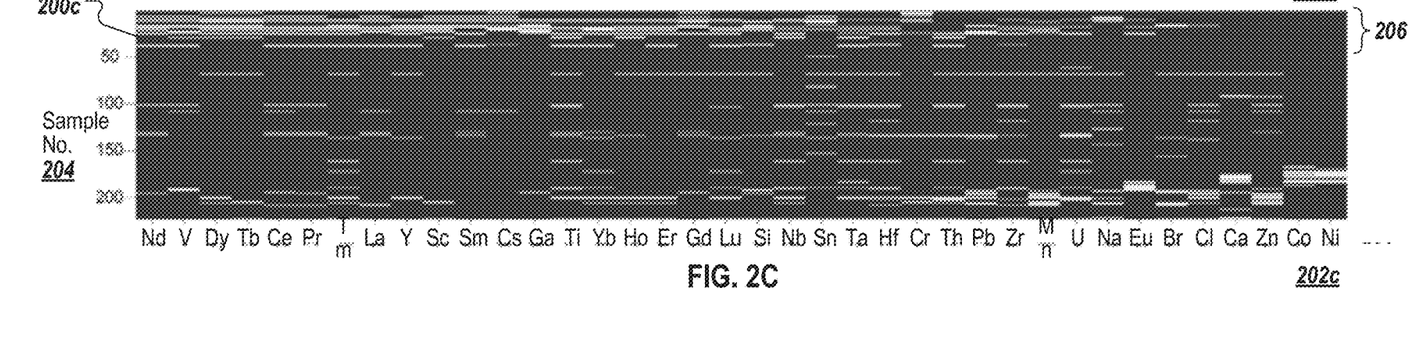

FIGS. 2A-2C are graphs 200*a*-200*c* showing elements detected at various depths, according to some implementations of the present disclosure. For example, FIG. 2A summarizes all geochemical elements within a specific well, with light lines indicating where significant profile changes exist. An X-axis 202*a* lists elements sorted according to their relative importance (for example, based on the number of boundaries identified). A Y-axis 204 represents a sample number, where each sample is related to a specific depth within a specific well. The samples that show a pattern of largely continuous light lines across the X-axis (for more than 50% of all samples) have a boundary detected for most of the elements, and those boundaries are considered greater-likelihood boundaries. The other samples show a pattern of discontinuous light lines, for example, indicating boundaries for some elements or no boundaries at all. Boundaries derived from patchy occurrences can be considered either as moderate- or low-likelihood boundaries.

Referring to FIG. 2B, elements in an X-axis 202*b* of the graph 200*b* are sorted (in descending order from left to right) by their sensitivity to changes for boundary identification. The elements in the graph 200*b* represent a subset of elements in the graph 200*a*. The elements included in FIG. 2B represent a subset of the elements in FIG. 2A that have greater ranking for boundary identification. In the graph 200*b*, light line segments show where boundaries have been identified, and dark line segments identify intra-boundary areas. Each sample is related with a specific depth within the specific well.

Referring to FIG. 2C, samples 206 are sorted in an X-axis 202*b* along a continuity of the boundary at the top of the graph 200*c*. Light lines show the existence of a boundary based on a specific element in a particular sample. The elements in FIG. 2C are the same subset of elements shown in FIG. 2B, but the data is sorted along a continuity of boundary information at the top of the graph 200*b*. The sorting results in an order of the elements shown in the graph 200*c*. In the graph 200*c*, light line segments show where boundaries have been. Each sample is related to a specific depth within a particular well.

In a fifth step, additional filtering and weighting can be applied for the remaining important elements and element ratios for boundary identification. To classify the boundaries in terms of importance, specific elements or ratios can be weighted based on their relative importance, for example, depending on lithology, mineralogy, and study objectives. Weighting of elements can vary in each study, meaning that elements will have different weights.

In some implementations, geologists can introduce manual weighting. The use of manual weighting can result in the removal of certain elements from the calculation of the derivatives. Manual weighting can be repeated for several elements and element ratios, for example, until sufficiently good results are achieved.

In some implementations, smaller weights can be assigned to the major elements (for example, Si, Al, K, Ca, Mg, and Mn) in order to avoid boundary identification based solely on lithology. Further, greater weights can be assigned to particular trace elements that are concentrated in heavy minerals (for example, Zr, Hf, Nb, Y, and Ta).

Figure 3:
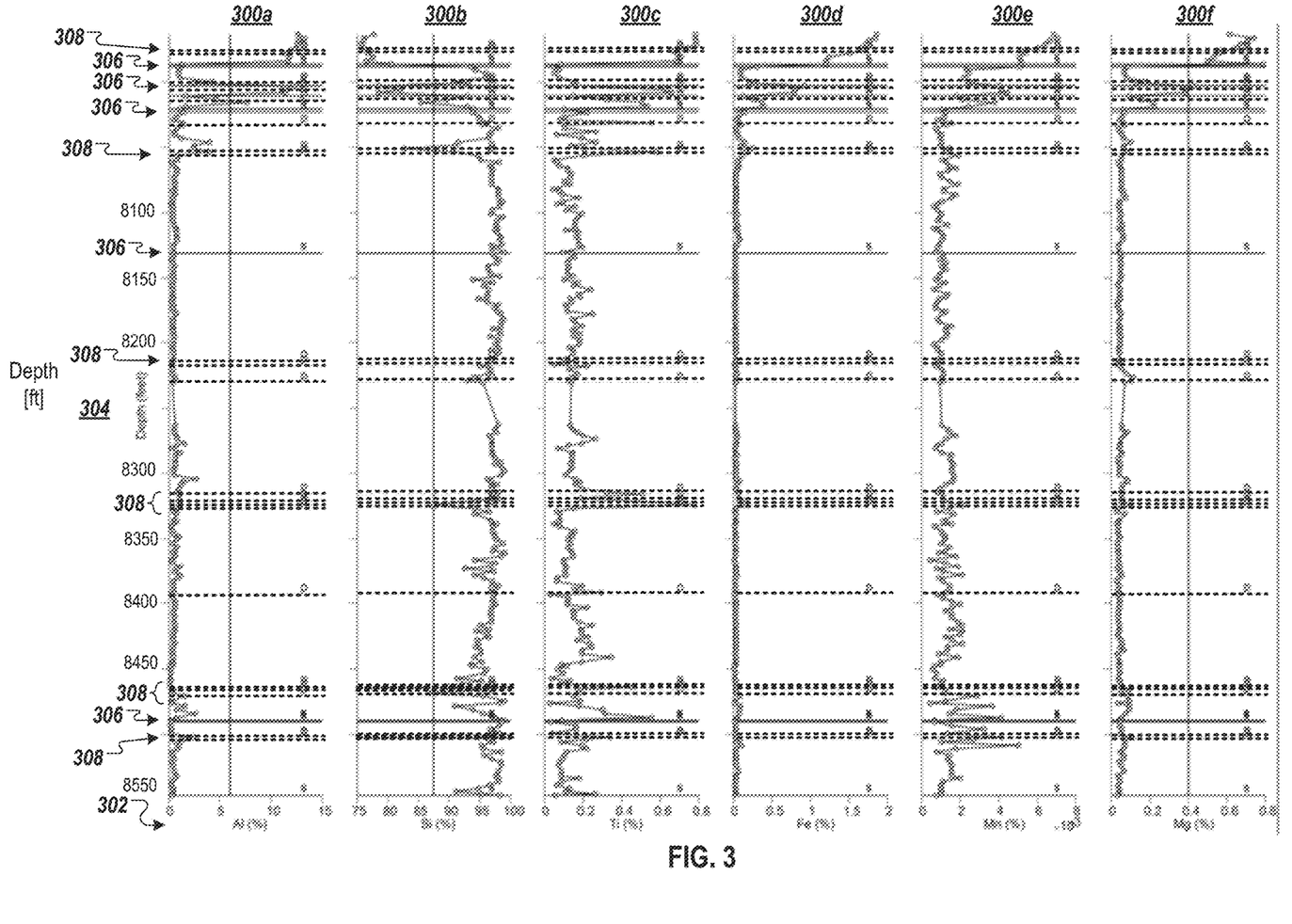
FIG. 3 is a set of graphs summarizing example results of the analysis including six elemental profiles and a prediction from the workflow in terms of greater-likelihood boundaries, according to some implementations of the present disclosure.

FIG. 3 is a set of graphs 300*a*-300*f* summarizing example results of the derivatives analysis including six elemental profiles and a prediction from the workflow in terms of greater-likelihood boundaries, according to some implementations of the present disclosure. For example, the graphs 300*a*-300*f* can be produced after applying the filters in steps 3, 4, and 5, and after summarizing the results. The graphs 300*a*-300*f* present element percentage data at different depths for six elemental profiles. An X-axis 302 that indicates element abundance is used to plot elemental abundance percentages against a Y-axis 304 of depth. This information can be used, for example, to make a prediction where boundaries are located from the workflow described. For example, two types of boundaries are shown in the graphs 300*a*-300*f*. First, solid lines 306 can indicate strong evidence of boundaries (for example, greater-likelihood boundaries) where changes have been detected at the same depth level for more than half of the elements after filtering processes have been applied. Second, dashed lines 308 can indicate moderate-likelihood boundaries associated with samples that, for example, exhibit changes in ≤50% and ≥20% of the samples.

Figure 4:
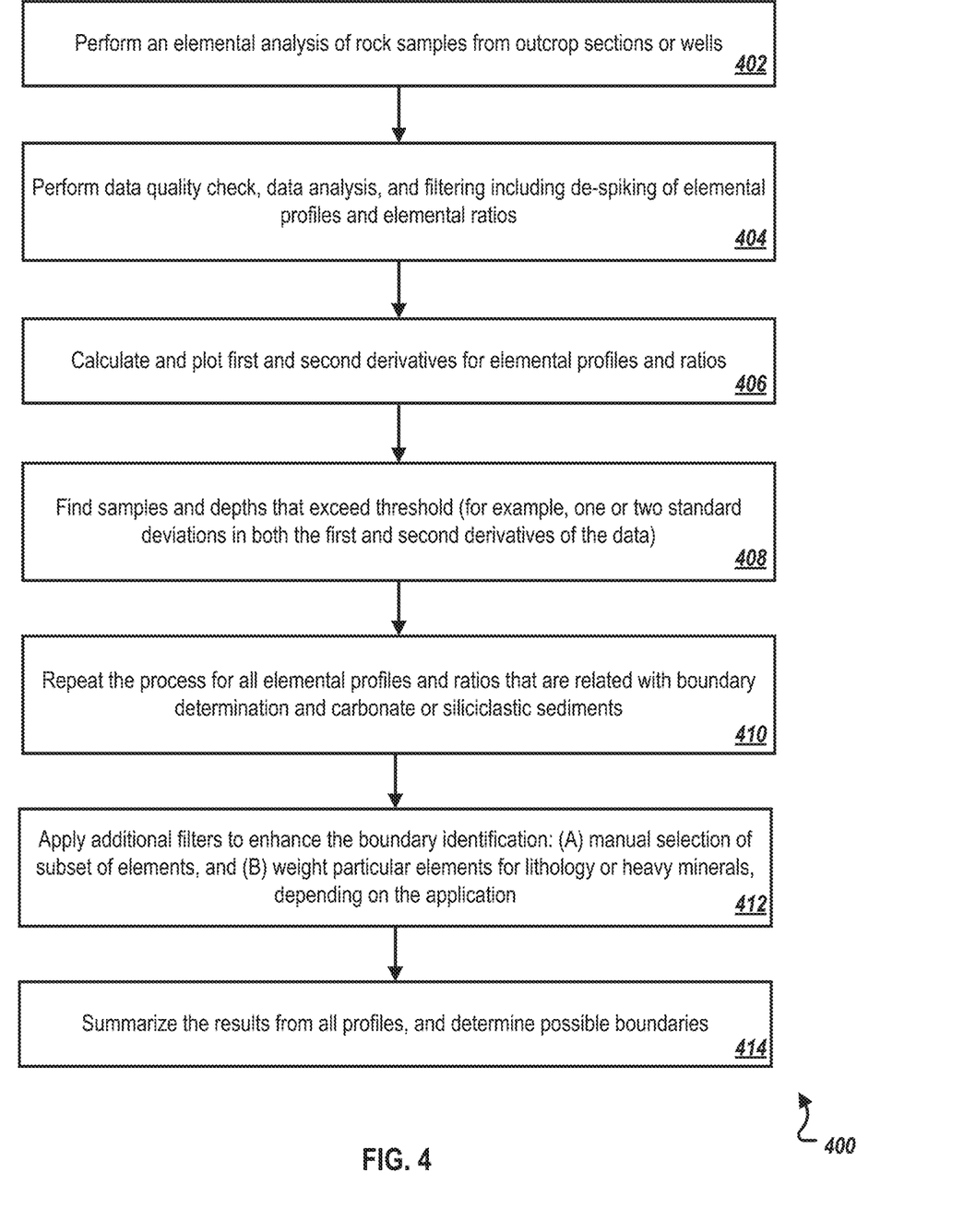
FIG. 4 is a flowchart showing an example of a workflow for statistical identification of boundaries, according to some implementations of the present disclosure.

FIG. 4 is a flowchart showing an example of a workflow 400 for statistical identification of boundaries, according to some implementations of the present disclosure. For example, the workflow 400 can facilitate a quick-look analysis of the data, allowing a prediction of locations of certain boundaries. The workflow 400 can be used, for example, to guide a geologist in a complete workflow for chemostratigraphy (FIG. 5).

At 402, elemental analysis is performed on rock samples at various depths in outcrops and wells. At 404, quality checking is performed on the samples, including de-spiking and normalization procedures. At 406, the first and second derivatives are calculated for elements and element ratio profiles. In some implementations, elemental profiles and ratios and 1st and 2nd derivative can be plotted, such as through automatic calculations, and presented to a user. At 408, samples and depths are identified that exceed a specific threshold, for example, one or two standard deviations from the median. At 410, the process of steps 402-408 can be repeated for all the elements and element ratios relevant to boundary identification in carbonate or siliciclastic rock successions (which can be study-dependent). At 412, additional filters can be applied to enhance boundary definition. For example, the filters can be chosen through: (i) manual selection of important elements based on other studies, and (ii) weighting of the relative importance of elements (for example, based on lithology or heavy mineral contents). Step 412 can be optional, for example, if a geologist knows which elements are important for a particular formation. At 414, the results from the profiles are summarized, and definite and possible boundaries are determined.

Figure 5:
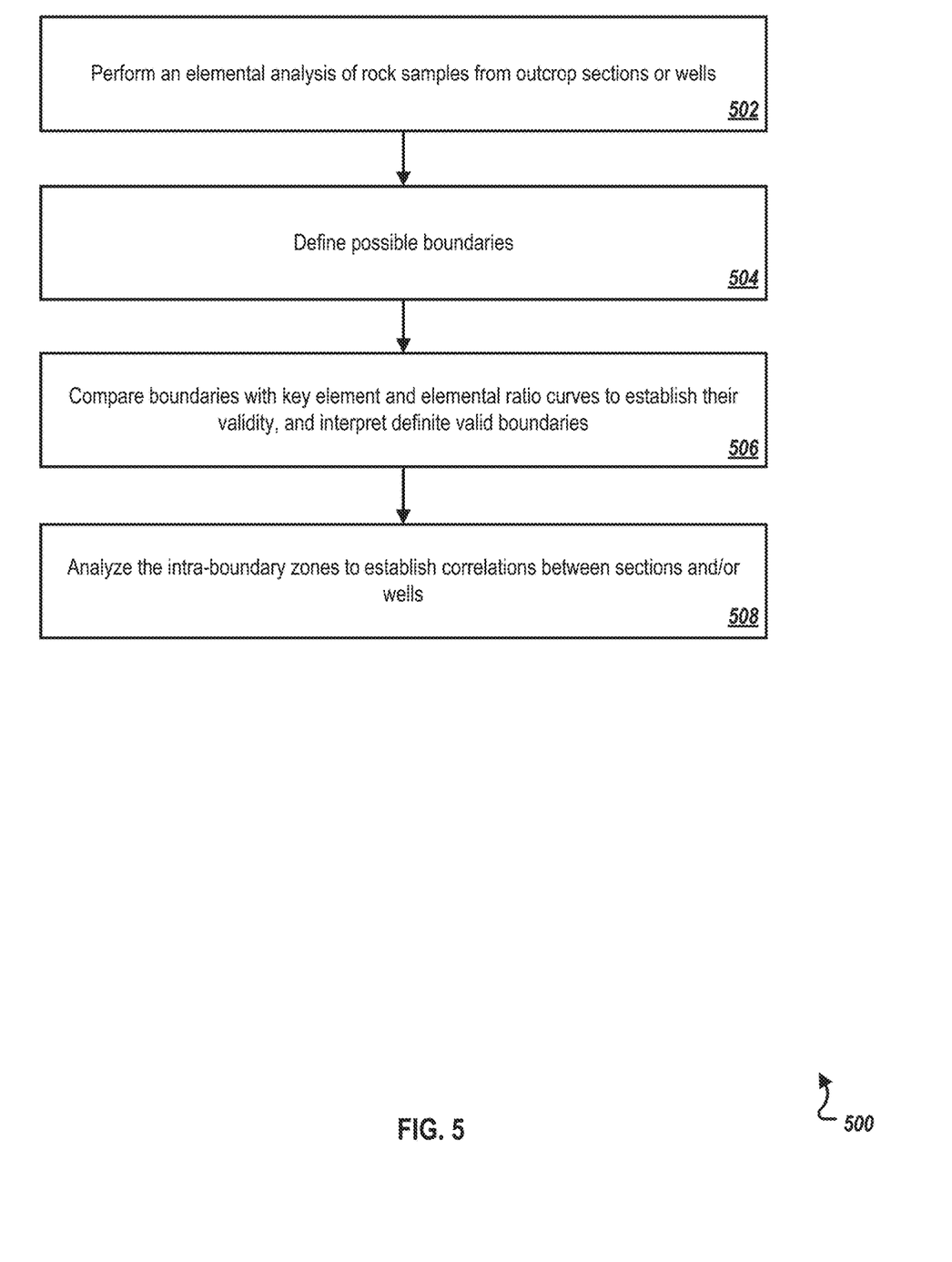
FIG. 5 is a flow chart of an example of a general chemostratigraphic workflow for boundary definition and correlation between wells including utilizing deviates for boundary identification, according to some implementations of the present disclosure.

FIG. 5 is a flow chart of an example of a general chemostratigraphic workflow 500 for boundary definition and correlation between wells including utilizing deviates for boundary identification, according to some implementations of the present disclosure. At 502, an elemental analysis of rock samples from outcrop sections or wells is performed. At 504, possible boundaries are defined according to workflow 400. At 506, boundaries are compared with element and elemental ratio curves, for example, to establish their validity and interpret definite valid boundaries. At 508, the intra-boundary zones are analyzed to establish correlations between sections or wells.

Figure 6:
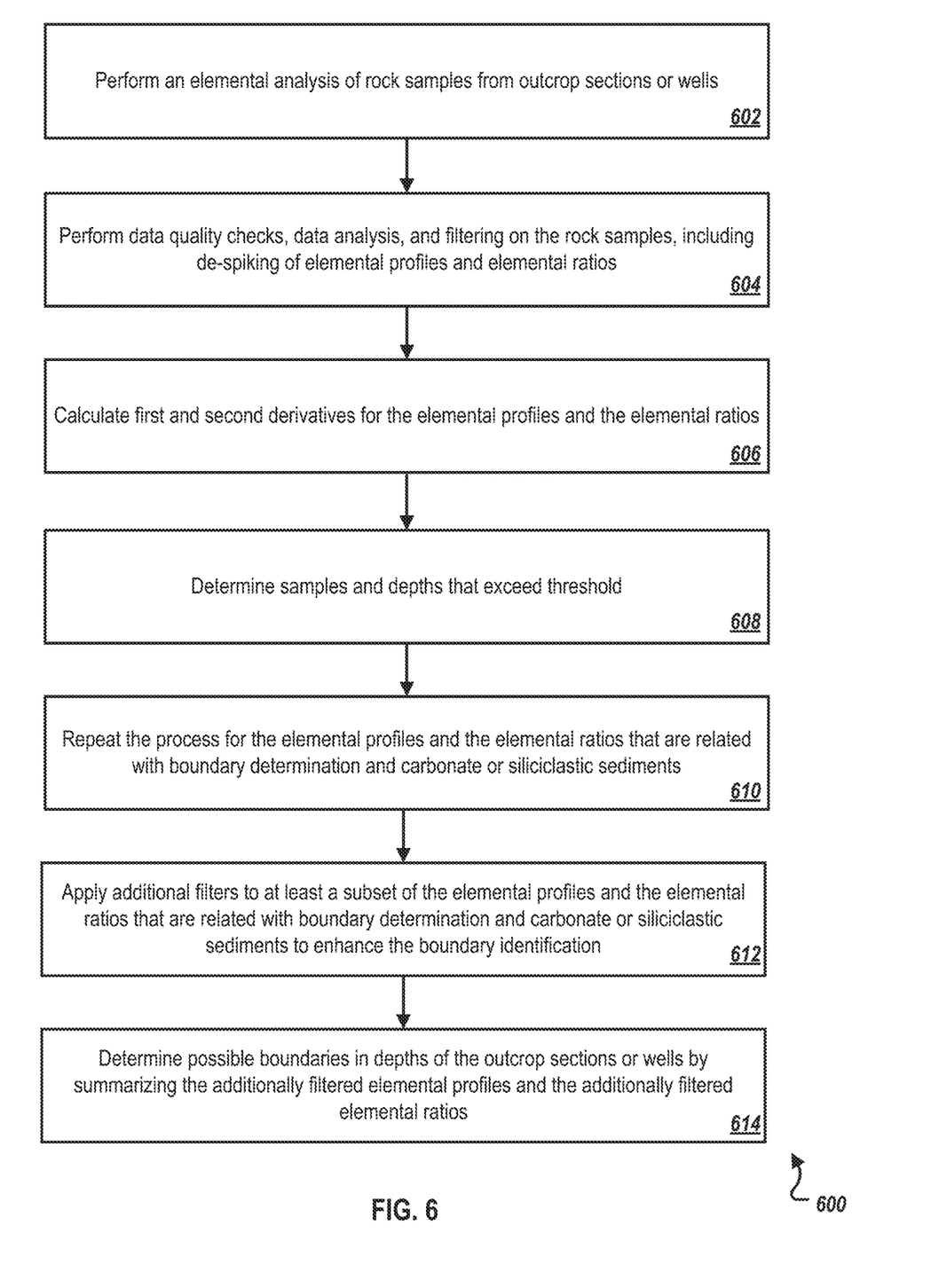
FIG. 6 is a flowchart of an example method for identifying geological boundaries based on first and second derivatives of elemental composition and elemental ratio profiles, according to some implementations of the present disclosure.

FIG. 6 is a flowchart of an example method 600 for identifying geological boundaries based on first and second derivatives of elemental composition and elemental ratio profiles, according to some implementations of the present disclosure. For clarity of presentation, the description that follows generally describes method 600 in the context of the other figures in this description. However, it will be understood that method 600 may be performed, for example, by any system, environment, software, and hardware, or a combination of systems, environments, software, and hardware. In some implementations, various steps of method 600 can be run in parallel, in combination, in loops, or in any order.

At 602, an elemental analysis of rock samples from outcrop sections or wells is performed. For example, rock samples can be collected for a group of elements, such as the elements listed along the X-axis 202*a*. From 602, method 600 proceeds to 604.

At 604, data quality checks, data analysis, and filtering are performed on the rock samples, including de-spiking of elemental profiles and elemental ratios. For example, outlier values for the samples can be discarded. From 604, method 600 proceeds to 606.

At 606, first and second derivatives for the elemental profiles and the elemental ratios are calculated. As an example, for a given element, first and second derivatives can be determined based on changes in values in FIG. 1A, such as those plotted in FIGS. 1B and 1C. From 606, method 600 proceeds to 608.

At 608, samples and depths that exceed threshold are determined. For example, samples that exceed one standard deviation from the median value of the first and second derivatives can be recorded as potential boundaries. From 608, method 600 proceeds to 610.

At 610, the process is repeated for the elemental profiles and the elemental ratios that are related with boundary determination and carbonate or siliciclastic sediments. For example, some or all of steps 602-608 can be repeated for other elements and elemental ratios. From 610, method 600 proceeds to 612.

At 612, additional filters are applied to at least a subset of the elemental profiles and the elemental ratios to enhance the boundary identification. For example, filters can be applied that are chosen through: (i) manual selection of important elements based on other studies, and (ii) weighting of the relative importance of elements (for example, based on lithology or heavy mineral contents). From 612, method 600 proceeds to 614.

At 614, possible boundaries in depths of the outcrop sections or wells are determined by summarizing the additionally filtered elemental profiles and the additionally filtered elemental ratios. For example, boundaries can be determined that are associated with the solid lines 306 and the dashed lines 308. From 614, method 600 stops.

Figure 7:
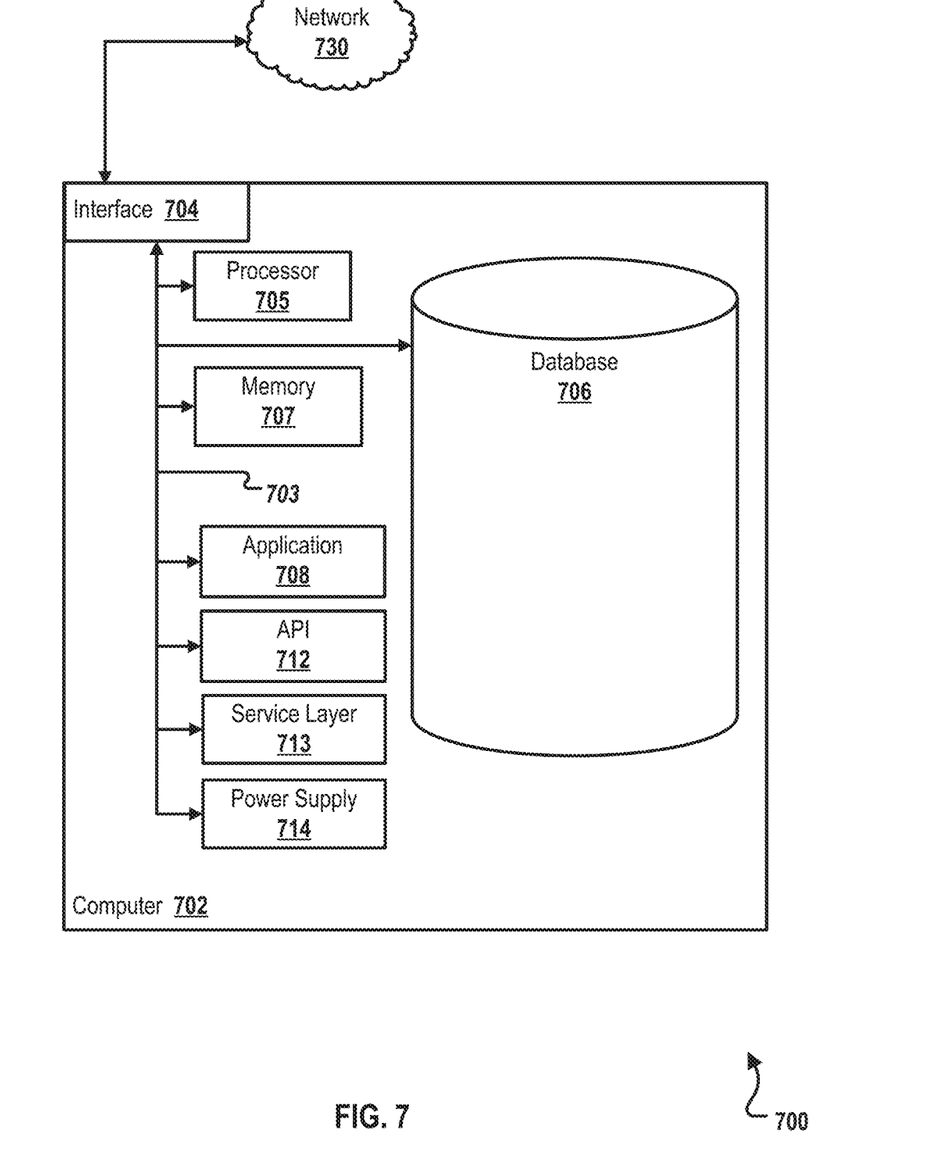
FIG. 7 is a block diagram illustrating an example computer system used to provide computational functionalities associated with described algorithms, methods, functions, processes, flows, and procedures as described in the instant disclosure, according to some implementations of the present disclosure.

FIG. 7 is a block diagram of an example computer system 700 used to provide computational functionalities associated with described algorithms, methods, functions, processes, flows, and procedures, as described in the instant disclosure, according to some implementations of the present disclosure. The illustrated computer 702 is intended to encompass any computing device such as a server, desktop computer, laptop/notebook computer, wireless data port, smart phone, personal data assistant (PDA), tablet computing device, one or more processors within these devices, or any other processing device, including physical or virtual instances (or both) of the computing device. Additionally, the computer 702 may comprise a computer that includes an input device, such as a keypad, keyboard, or touch screen that can accept user information, and an output device that conveys information associated with the operation of the computer 702, including digital data, visual, or audio information (or a combination of information), or a graphical-type user interface (UI) (or GUI).

The computer 702 can serve in a role as a client, network component, a server, a database, a persistency, or any other component (or a combination of roles) of a computer system for performing the subject matter described in the instant disclosure. The illustrated computer 702 is communicably coupled with a network 730. In some implementations, one or more components of the computer 702 may be configured to operate within environments, including cloud-computing-based, local, or global environment (or a combination of environments).

The computer 702 is an electronic computing device operable to receive, transmit, process, store, or manage data and information associated with the described subject matter. According to some implementations, the computer 702 may also include or be communicably coupled with an application server, email server, web server, caching server, or streaming data server (or a combination of servers).

The computer 702 can receive requests over network 730 from a client application (for example, executing on another computer 702) and respond to the received requests by processing the received requests using software applications. In addition, requests may also be sent to the computer 702 from internal users (for example, from a command console or another access method), external or third-parties, other automated applications, as well as entities, individuals, systems, or computers.

Each of the components of the computer 702 can communicate using a system bus 703. In some implementations, any or all of the components of the computer 702, hardware or software (or a combination of both hardware and software), may interface with each other or the interface 704 (or a combination of both), over the system bus 703 using an application programming interface (API) 712 or a service layer 713 (or a combination of the API 712 and service layer 713). The API 712 may include specifications for routines, data structures, and object classes. The API 712 may be either computer-language independent or dependent and refer to a complete interface, a single function, or even a set of APIs. The service layer 713 provides software services to the computer 702 and other components (whether or not illustrated) that are communicably coupled to the computer 702. The functionality of the computer 702 may be accessible for all service consumers using this service layer. Software services, such as those provided by the service layer 713, provide reusable, defined functionalities through a defined interface. For example, the interface may be software written in JAVA, C++, or another language providing data in extensible markup language (XML) format. While illustrated as an integrated component of the computer 702, alternative implementations may illustrate the API 712 or the service layer 713 as stand-alone components in relation to other components of the computer 702 and other components (whether or not illustrated) that are communicably coupled to the computer 702. Moreover, any or all parts of the API 712 or the service layer 713 may be implemented as child or sub-modules of another software module, enterprise application, or hardware module without departing from the scope of this disclosure.

The computer 702 includes an interface 704. Although illustrated as a single interface 704 in FIG. 7, two or more interfaces 704 may be used according to particular needs, desires, or particular implementations of the computer 702. The interface 704 is used by the computer 702 for communicating with other systems that are connected to the network 730 (whether illustrated or not) in a distributed environment. Generally, the interface 704 comprises logic encoded in software or hardware (or a combination of software and hardware) and is operable to communicate with the network 730. More specifically, the interface 704 may comprise software supporting one or more communication protocols associated with communications such that the network 730 or interface's hardware is operable to communicate physical signals within and outside of the illustrated computer 702.

The computer 702 includes a processor 705. Although illustrated as a single processor 705 in FIG. 7, two or more processors may be used according to particular needs, desires, or particular implementations of the computer 702. Generally, the processor 705 executes instructions and manipulates data to perform the operations of the computer 702 and any algorithms, methods, functions, processes, flows, and procedures as described in the instant disclosure.

The computer 702 also includes a database 706 that can hold data for the computer 702 and other components (or a combination of both) that can be connected to the network 730 (whether illustrated or not). For example, database 706 can be an in-memory or conventional database storing data consistent with this disclosure. In some implementations, database 706 can be a combination of two or more different database types (for example, a hybrid in-memory and conventional database) according to particular needs, desires, or particular implementations of the computer 702 and the described functionality. Although illustrated as a single database 706 in FIG. 7, two or more databases (of the same or combination of types) can be used according to particular needs, desires, or particular implementations of the computer 702 and the described functionality. While database 706 is illustrated as an integral component of the computer 702, in alternative implementations, database 706 can be external to the computer 702.

The computer 702 also includes a memory 707 that can hold data for the computer 702 and other components (or a combination of both) that can be connected to the network 730 (whether illustrated or not). Memory 707 can store any data consistent with this disclosure. In some implementations, memory 707 can be a combination of two or more different types of memory (for example, a combination of semiconductor and magnetic storage) according to particular needs, desires, or particular implementations of the computer 702 and the described functionality. Although illustrated as a single memory 707 in FIG. 7, two or more memories 707 (of the same or combination of types) can be used according to particular needs, desires, or particular implementations of the computer 702 and the described functionality. While memory 707 is illustrated as an integral component of the computer 702, in alternative implementations, memory 707 can be external to the computer 702.

The application 708 is an algorithmic software engine providing functionality according to particular needs, desires, or particular implementations of the computer 702, particularly with respect to functionality described in this disclosure. For example, application 708 can serve as one or more components, modules, or applications. Further, although illustrated as a single application 708, the application 708 may be implemented as multiple applications 708 on the computer 702. In addition, although illustrated as integral to the computer 702, in alternative implementations, the application 708 can be external to the computer 702.

The computer 702 can also include a power supply 714. The power supply 714 can include a rechargeable or non-rechargeable battery that can be configured to be either user- or non-user-replaceable. In some implementations, the power supply 714 can include power-conversion or management circuits (including recharging, standby, or a different power management functionality). In some implementations, the power-supply 714 can include a power plug to allow the computer 702 to be plugged into a wall socket to, for example, power the computer 702 or recharge a rechargeable battery.

There may be any number of computers 702 associated with, or external to, a computer system containing computer 702, each computer 702 communicating over network 730. Further, the term "client," "user," and other terminology may be used interchangeably without departing from the scope of this disclosure. Moreover, this disclosure contemplates that many users may use one computer 702, or that one user may use multiple computers 702.

Described implementations of the subject matter can include one or more features, alone or in combination.

For example, in a first implementation, a computer-implemented method, comprising the following. An elemental analysis of rock samples from outcrop sections or wells is performed. Data quality checks, data analysis, and filtering are performed on the rock samples, including de-spiking of elemental profiles and elemental ratios. First and second derivatives for the elemental profiles and the elemental ratios are calculated. Samples and depths that exceed thresholds are determined. The process is repeated for the elemental profiles and the elemental ratios that are related with boundary determination and carbonate or siliciclastic sediments. Additional filters are applied to at least a subset of the elemental profiles and elemental ratios that are related with boundary determination and carbonate or siliciclastic sediments to enhance the boundary identification. Possible boundaries in depths of the outcrop sections or wells are determined by summarizing the additionally filtered elemental profiles and the additionally filtered elemental ratios.

The foregoing and other described implementations can each, optionally, include one or more of the following features:

A first feature, combinable with any of the following features, the threshold is one or two standard deviations in both the first and second derivatives.

A second feature, combinable with any of the previous or following features, the method further comprising receiving a manual selection of subset of elements and weighting particular elements for lithology or heavy minerals.

A third feature, combinable with any of the previous or following features, determining a possible boundary for a given element or a given element ratio includes analyzing an abundance of specific boundaries for given element or a given element ratio to determine whether a boundary is definite or not.

A fourth feature, combinable with any of the previous or following features, the method further comprising filtering to exclude certain elements and weighting certain elements according to a sensitivity to boundary identification and elements that are based on lithology or certain minerals for more precise boundary selection.

A fifth feature, combinable with any of the previous or following features, the method further comprising determining confident and potential boundaries.

A sixth feature, combinable with any of the previous or following features, the method further comprising comparing boundaries with element and elemental ratio curves to establish a validity of the boundaries and interpret definite valid boundaries; and analyzing intra-boundary zones to establish correlations between sections or wells.

In a second implementation, a non-transitory, computer-readable medium storing one or more instructions executable by a computer system to perform operations comprising the following. An elemental analysis of rock samples from outcrop sections or wells is performed. Data quality checks, data analysis, and filtering are performed on the rock samples, including de-spiking of elemental profiles and elemental ratios. First and second derivatives for the elemental profiles and the elemental ratios are calculated. Samples and depths that exceed thresholds are determined. The process is repeated for the elemental profiles and the elemental ratios that are related with boundary determination and carbonate or siliciclastic sediments. Additional filters are applied to at least a subset of the elemental profiles and elemental ratios that are related with boundary determination and carbonate or siliciclastic sediments to enhance the boundary identification. Possible boundaries in depths of the outcrop sections or wells are determined by summarizing the additionally filtered elemental profiles and the additionally filtered elemental ratios.

The foregoing and other described implementations can each, optionally, include one or more of the following features:

A first feature, combinable with any of the following features, the threshold is one or two standard deviations in both the first and second derivatives.

A second feature, combinable with any of the previous or following features, the operations further comprising receiving a manual selection of subset of elements and weighting particular elements for lithology or heavy minerals.

A third feature, combinable with any of the previous or following features, determining a possible boundary for a given element or a given element ratio includes analyzing an abundance of specific boundaries for given element or a given element ratio to determine whether a boundary is definite or not.

A fourth feature, combinable with any of the previous or following features, the operations further comprising filtering to exclude certain elements and weighting certain elements according to a sensitivity to boundary identification and elements that are based on lithology or certain minerals for more precise boundary selection.

A fifth feature, combinable with any of the previous or following features, the operations further comprising determining confident and potential boundaries.

A sixth feature, combinable with any of the previous or following features, the operations further comprising comparing boundaries with element and elemental ratio curves to establish a validity of the boundaries and interpret definite valid boundaries; and analyzing intra-boundary zones to establish correlations between sections or wells or both.

In a third implementation, a computer-implemented system. The system includes one or more processors. The system also includes a non-transitory computer-readable storage medium coupled to the one or more processors and storing programming instructions for execution by the one or more processors. The programming instructions instruct the one or more processors to perform operations comprising the following. An elemental analysis of rock samples from outcrop sections or wells is performed. Data quality checks, data analysis, and filtering are performed on the rock samples, including de-spiking of elemental profiles and elemental ratios. First and second derivatives for the elemental profiles and the elemental ratios are calculated. Samples and depths that exceed thresholds are determined. The process is repeated for the elemental profiles and the elemental ratios that are related with boundary determination and carbonate or siliciclastic sediments. Additional filters are applied to at least a subset of the elemental profiles and elemental ratios that are related with boundary determination and carbonate or siliciclastic sediments to enhance the boundary identification. Possible boundaries in depths of the outcrop sections or wells are determined by summarizing the additionally filtered elemental profiles and the additionally filtered elemental ratios.

The foregoing and other described implementations can each, optionally, include one or more of the following features:

A first feature, combinable with any of the following features, the threshold is one or two standard deviations in both the first and second derivatives.

A second feature, combinable with any of the previous or following features, the operations further comprising receiving a manual selection of subset of elements and weighting particular elements for lithology or heavy minerals.

A third feature, combinable with any of the previous or following features, determining a possible boundary for a given element or a given element ratio includes analyzing an abundance of specific boundaries for given element or a given element ratio to determine whether a boundary is definite or not.

A fourth feature, combinable with any of the previous or following features, the operations further comprising filtering to exclude certain elements and weighting certain elements according to a sensitivity to boundary identification and elements that are based on lithology or certain minerals for more precise boundary selection.

A fifth feature, combinable with any of the previous or following features, the operations further comprising determining confident and potential boundaries.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include special purpose logic circuitry, for example, a central processing unit (CPU), a field programmable gate array (FPGA), or an application-specific integrated circuit (ASIC). In some implementations, the data processing apparatus or special purpose logic circuitry (or a combination of the data processing apparatus or special purpose logic circuitry) may be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, IOS, or any other conventional operating system.

A computer program, which may also be referred to or described as a program, software, a software application, a module, a software module, a script, or code can be written in any form of programming language. A computer program can include compiled or interpreted languages, or declarative or procedural languages. A computer program can be deployed in any form, including as a stand-alone program or as a module, component, or subroutine for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or processes, the programs may instead include a number of sub-modules, third-party services, components, or libraries. Conversely, the features and functionality of various components can be combined into single components. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers that can be used for the execution of a computer program can be based on general or special purpose microprocessors, both, or any other kind of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory) for storing computer program instructions and data includes all forms of permanent/non-permanent or volatile/non-volatile memory, media and memory devices, including by way of example semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices; magnetic devices, for example, tape, cartridges, cassettes, internal/removable disks; magneto-optical disks; and optical memory devices, for example, digital video disc (DVD), CD-ROM, DVD+/-R, DVD-RAM, DVD-ROM, HD-DVD, and BLURAY, and other optical memory technologies. The memory may store various objects or data, including caches, classes, frameworks, applications, modules, backup data, jobs, web pages, web page templates, data structures, database tables, repositories storing dynamic information, and any other information including any parameters, variables, algorithms, instructions, rules, constraints, or references. Additionally, the memory may include any other data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, for example, a cathode ray tube (CRT), liquid crystal display (LCD), light emitting diode (LED), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity, or a multi-touch screen using capacitive or electric sensing. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons. These and other UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with some implementations of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20), all or a portion of the Internet, or any other communication system or systems at one or more locations (or a combination of communication networks). The network may communicate with, for example, Internet Protocol (IP) packets, Frame Relay frames, Asynchronous Transfer Mode (ATM) cells, voice, video, or data (or a combination of communication types) between network addresses.

The computing system can include clients and servers. A client and server are generally remote from each other and typically interact through a communication network. The relationship of client and server arises by virtue of computer programs running on the respective computers and having a client-server relationship to each other.

Cluster file system involved in the present disclosure can be any file system type accessible from multiple servers for read and update. Locking or consistency tracking is not necessary since the locking of exchange file system can be done at application layer. Furthermore, Unicode data files are different from non-Unicode data files.

While this specification contains many specific implementation details, these should not be construed as limitations on the scope of the present disclosure or on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain this disclosure. Other changes, substitutions, and alterations are also possible without departing from the spirit and scope of this disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A computer-implemented method, comprising:
   performing an elemental analysis of data associated with rock samples from outcrop sections or wells;
   performing data quality checks, data analysis, and filtering on the rock samples, including removing outliers and de-spiking of elemental profiles and elemental ratios of combinations of elements;
   calculating first and second derivatives for the elemental profiles and the elemental ratios;
   determining samples and depths that exceed a threshold by comparing the calculated first and second derivatives to the threshold, wherein the threshold for identifying a boundary as fit for a particular study is two standard deviations from the median (or mean) in both the first and second derivatives;
   repeating performing the elemental analysis, performing the data quality checks, data analysis, and filtering, calculating first and second derivatives of the elemental profiles and the elemental ratios from well logs, and determining samples and depths for the elemental profiles and the elemental ratios that are relevant to boundary identification and carbonate or siliciclastic sediments;
   applying additional filters to at least a subset of the elemental profiles and the elemental ratios, the subset including elemental profiles that are relevant to the boundary identification and carbonate or siliciclastic sediments to enhance the boundary identification; and
   determining, by summarizing the additionally filtered elemental profiles and the additionally filtered elemental ratios and using first and second derivatives for the elemental profiles and the elemental ratios, possible boundaries in depths of the outcrop sections or wells.

2. The computer-implemented method of claim 1, further comprising receiving a manual selection of subset of elements and weighting particular elements for lithology or heavy minerals.

3. The computer-implemented method of claim 1, wherein determining a possible boundary for a given element or a given element ratio includes analyzing specific boundaries for given element or a given element ratio to determine whether a boundary is definite or not.

4. The computer-implemented method of claim 1, further comprising filtering to exclude certain elements and weighting certain elements according to a sensitivity to boundary identification and elements that are based on lithology or certain minerals for more precise boundary selection.

5. The computer-implemented method of claim 1, further comprising:
   comparing boundaries with element and elemental ratio curves to establish a validity of the boundaries and interpret definite valid boundaries; and
   analyzing intra-boundary zones to establish correlations between sections and/or wells.

6. A non-transitory, computer-readable medium storing one or more instructions executable by a computer system to perform operations comprising:
   performing an elemental analysis of data associated with rock samples from outcrop sections or wells;
   performing data quality checks, data analysis, and filtering on the rock samples, including removing outliers and de-spiking of elemental profiles and elemental ratios of combinations of elements;
   calculating first and second derivatives for the elemental profiles and the elemental ratios;

determining samples and depths that exceed a threshold by comparing the calculated first and second derivatives to the threshold, wherein the threshold for identifying a boundary as fit for a particular study is two standard deviations from the median (or mean) in both the first and second derivatives;

repeating performing the elemental analysis, performing the data quality checks, data analysis, and filtering, calculating first and second derivatives of the elemental profiles and the elemental ratios from well logs, and determining samples and depths for the elemental profiles and the elemental ratios that are relevant to boundary identification and carbonate or siliciclastic sediments;

applying additional filters to at least a subset of the elemental profiles and the elemental ratios, the subset including elemental profiles that are relevant to the boundary identification and carbonate or siliciclastic sediments to enhance the boundary identification; and determining, by summarizing the additionally filtered elemental profiles and the additionally filtered elemental ratios and using first and second derivatives for the elemental profiles and the elemental ratios, possible boundaries in depths of the outcrop sections or wells.

7. The non-transitory, computer-readable medium of claim 6, the operations further comprising receiving a manual selection of subset of elements and weighting particular elements for lithology or heavy minerals.

8. The non-transitory, computer-readable medium of claim 6, wherein determining a possible boundary for a given element or a given element ratio includes analyzing specific boundaries for given element or a given element ratio to determine whether a boundary is definite or not.

9. The non-transitory, computer-readable medium of claim 6, the operations further comprising filtering to exclude certain elements and weighting certain elements according to a sensitivity to boundary identification and elements that are based on lithology or certain minerals for more precise boundary selection.

10. The non-transitory, computer-readable medium of claim 6, the operations further comprising:
comparing boundaries with element and elemental ratio curves to establish a validity of the boundaries and interpret definite valid boundaries; and
analyzing intra-boundary zones to establish correlations between sections and/or wells.

11. A computer-implemented system, comprising:
one or more processors; and
a non-transitory computer-readable storage medium coupled to the one or more processors and storing programming instructions for execution by the one or more processors, the programming instructions instruct the one or more processors to perform operations comprising:
performing an elemental analysis of data associated with rock samples from outcrop sections or wells;
performing data quality checks, data analysis, and filtering on the rock samples, including removing outliers and de-spiking of elemental profiles and elemental ratios of combinations of elements;
calculating first and second derivatives for the elemental profiles and the elemental ratios;
determining samples and depths that exceed a threshold by comparing the calculated first and second derivatives to the threshold, wherein the threshold for identifying a boundary as fit for a particular study is two standard deviations from the median (or mean) in both the first and second derivatives;
repeating performing the elemental analysis, performing the data quality checks, data analysis, and filtering, calculating first and second derivatives of the elemental profiles and the elemental ratios from well logs, and determining samples and depths for the elemental profiles and the elemental ratios that are relevant to boundary identification and carbonate or siliciclastic sediments;
applying additional filters to at least a subset of the elemental profiles and the elemental ratios, the subset including elemental profiles that are relevant to the boundary identification and carbonate or siliciclastic sediments to enhance the boundary identification; and
determining, by summarizing the additionally filtered elemental profiles and the additionally filtered elemental ratios and using first and second derivatives for the elemental profiles and the elemental ratios, possible boundaries in depths of the outcrop sections or wells.

12. The computer-implemented system of claim 11, the operations further comprising receiving a manual selection of subset of elements and weighting particular elements for lithology or heavy minerals.

13. The computer-implemented system of claim 11, wherein determining a possible boundary for a given element or a given element ratio includes analyzing specific boundaries for given element or a given element ratio to determine whether a boundary is definite or not.

14. The computer-implemented system of claim 11, the operations further comprising filtering to exclude certain elements and weighting certain elements according to a sensitivity to boundary identification and elements that are based on lithology or certain minerals for more precise boundary selection.

* * * * *